United States Patent [19]
Butler

[11] 4,212,980
[45] Jul. 15, 1980

[54] 5-PHENOXY-2-PYRIDINECARBONITRILE COMPOUNDS AND METHODS FOR THEIR PRODUCTION

[75] Inventor: Donald E. Butler, Ann Arbor, Mich.

[73] Assignee: Warner-Lambert Company, Morris Plains, N.J.

[21] Appl. No.: 960,323

[22] Filed: Nov. 13, 1978

[51] Int. Cl.$^2$ .......................................... C07D 213/57
[52] U.S. Cl. .................................... 546/288; 424/263
[58] Field of Search ........................................ 546/288

[56] References Cited
PUBLICATIONS

Villani et al., Journal of Medicinal Chemistry, vol. 18(1) pp. 1-8 1975.

*Primary Examiner*—Alan L. Rotman
*Attorney, Agent, or Firm*—Stephen Raines; David B. Ehrlinger; Frank S. Chow

[57] ABSTRACT

5-phenoxy-2-pyridinecarbonitrile compounds, which are useful as pharmacological agents, especially as agents for the reversal of amnesia, and methods for their preparation are disclosed. Pharmaceutical compositions containing said compounds and methods for using said compositions in treating senility and reversal of amnesia are also taught.

2 Claims, No Drawings

5-PHENOXY-2-PYRIDINECARBONITRILE COMPOUNDS AND METHODS FOR THEIR PRODUCTION

SUMMARY AND DETAILED DESCRIPTION

The present invention relates to new 5-phenoxy-2-pyridinecarbonitrile compounds. More particularly, the invention relates to new compounds of the formula

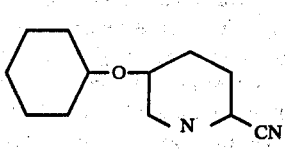

I and pharmaceutically-acceptable salts thereof and to methods for the production of the foregoing compounds.

The term "pharmaceutically-acceptable salt" is intended to mean a relatively non-toxic acid addition salt, such as the hydrochloride, sulfate [two equivalents of pyridinium compound would be coupled to a sulfate moiety], acetate, benzoate, etc.

In accordance with the invention, the foregoing compounds of formula I can be prepared by reacting a compound of the formula

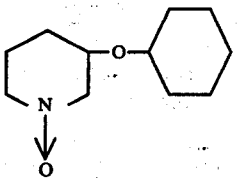

II with an alkylating agent, such as dimethylsulfate, diethylsulfate, trimethyloxonium tetrafluoroborate, triethyloxonium tetrafluoroborate, methylbromide or methyliodide; preferably dimethylsulfate; followed by treatment with an alkali metal cyanide, preferably sodium cyanide. Prior to the addition of the alkali metal cyanide an intermediate compound is formed, which is not isolated, having the structure

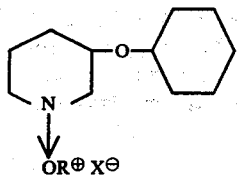

III where R⊕ is a carbonium ion derived from the alkylating agent. The pharmaceutically-acceptable salts are prepared by adjusting the pH.

The first step is conducted preferably in the absence of solvent, although a halogenated hydrocarbon may be employed (dichloromethane, tetrachloroethane or dichlorobenzene). The reactants are present in about equimolar amounts although a slight excess of aklylating agent is preferred.

The first step of the reaction is carried out at a temperature range of 25° C. to 100° C. for periods of from one to 10 hrs, preferably 95° to 100° C. for from three to four hrs.

The second step is carried out in water in an inert atmosphere using an excess of alkali metal cyanide.

The second step of the reaction is carried out at a temperature range of −5° C. to 30° C. for periods of from one to 24 hours, preferably −5° C. to 5° C. for periods of from four to six hours.

The product may be isolated as the free base by distillation or crystallization or as an acid addition salt by suitable adjustment of pH.

The necessary starting material of formulae II is a known compound.

A second process for the preparation of compounds of the invention requires the treatent of a compound of the formula

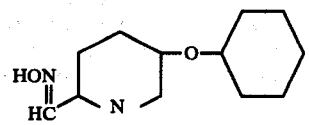

IV with a dehydrating agent. The product may be isolated in the form of a free base or treated with the appropriate acid to give rise to the desired acid-addition salt.

An excess of a dehydrating agent, such as thionyl chloride, phosphorus pentachloride, phosphorus oxychloride, acetic anhydride may be used, preferably thionyl chloride and a relatively inert organic solvent such as a chlorinated hydrocarbon (dichloromethane, tetrachlorethane, o-dichlorobenzene, etc.) or aromatic compound (benzene, toluene, etc.)

The reaction is carried out at a temperature range of 25° C. to 120° C. for periods of from one-half to 16 hrs, preferably 90° C. to 110° C. for about two hrs to eight hrs.

The product may be isolated by distillation or crystallization and converted to the appropriate acid-addition salt.

The necessary starting material IV and salts thereof are also part of the invention and method of preparation of compound IV is described in the experimental section.

The compounds of the invention may exist in anhydrous form as well as in solvated, including hydrated, forms. In general, the hydrated forms and the solvated forms with pharmaceutically-acceptable solvents are equivalent to the anhydrous or unsolvated form for the purposes of the invention.

Also in accordance with the invention, pharmaceutical compositions may be produced by formulating the compounds of formula I in dosage unit form with a pharmaceutical carrier. Some examples of dosage unit forms are tablets, capsules, lozenges, and pills; as well as powders and aqueous and non-aqueous solutions and suspensions packaged in containers containing either one or some larger number of dosage units and capable of being sub-divided into individual doses by such means as measurement into teaspoon or other standard container. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerine, sorbitol; polyethylene glycol; water; agar; alginic acid; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primarily liquid composition. The most satisfactory compositions are those in which a much higher proportion of the active ingredient is present. The compositions of the invention preferably contain from 1 to 500 mg, preferably 5 to 100 mg of the active ingredient per dosage unit is that the entire amount to be administered during a day can be made up from a reasonable number of dosage units.

The compounds of formula I may be incorporated into formulations intended for parenteral administration. Such compositions may be in a powdered form intended to be combined with an isotonic solution containing other ingredients such as preservatives, etc. or may be initially formulated as part of an isotonic solution which may contain preservatives, other active ingredients, etc.

The compounds of the invention are new chemical compounds of value as pharmacological agents. The compounds find use in the treatment of induced amnesia. The compounds of the invention generally would be administered to mammals in a dosage range of from about 0.014 to about 21.4 mg per kg of body weight per day, preferably 0.36 to 10.7 mg per kg per day. Thus 1 mg to 1500 mg, preferably 25 mg to 750 mg, are administered to a 70 kg host per day.

The effectiveness of the aforementioned compounds is determined by the following test. This test is designed to show the compound's ability to reverse amnesia produced by electroconvulsive shock.

One hundred male mice (Carworth, CF-1 strain, 19-21 g at time of shipment) are divided into five groups of 20 mice each. Each mouse is placed, one at a time, on a small shelf attached to the outside wall of a test box. In this position the mouse is suspended in space. Therefore, the mouse is motivated to step from the shelf through a conveniently placed small hole into the interior of the box. As soon as the mouse has all four feet within the semidarkened interior of the box, the grid floor of the box is electrified (1.5 milliamps, 3 second duration) to produce a strong pain-fear reaction from the animal. About five seconds thereafter, the mouse is removed from the test box and placed in a group holding cage.

Two hours after the above training the mice are given a single electroconvulsive shock produced by 20 miliamps delivered for 0.5 seconds through the ears. Immediately thereafter, the mice are returned to the holding cage.

Two hours after the convulsive treatment, the mice are injected intraperitoneally with the chemical being assesed. Usually three doses of the chemical will be tested at a time.

One hour after the drug treatment, the mice are tested for memory of the painful foot shock received within the self-box apparatus. This testing is accomplished by once again placing each mouse on the small shelf attached to the test box. Any mouse that stays on the shelf for 60 seconds without entering the box is counted as remembering the painful foot shock received within the box five hours earlier. Any mouse entering the box within the 60-second period is counted as having amnesia for the painful event.

Using this 60-second criterion, appropriate control experiments show (1.) 100 percent of mice will enter the box if no foot shock is delivered during the original training, (painful foot shock is necessary if the mice are to develop an aversion to entering the test box) (2.) 100 percent of mice will enter the box under the foregoing conditions even when treated with electroconvulsive shock at the three-hour point prior to testing (electroconvulsive shock treatment itself does not generate a fear of entering the test box).

The five groups of mice are treated as follows:

| Group | |
|---|---|
| (1) Ceiling Control Group: | Placebo |
| (2) Base Line Control Group: | Electroconvulsive shock, Placebo |
| (3) 1st Drug Dose Group: | Electroconvulsive shock, 5-Phenoxy-2-pyridinecarbonitrile |
| (4) 2nd Drug Dose Group: | Electroconvulsive shock, 5-Phenoxy-2-pyridinecarbonitrile |
| (5) 3rd Drug Dose Group: | Electroconvulsive shock, 5-Phenoxy-2-pyridinecarbonitrile |

The percentage of amnesia reversal is determined as follows for each drug group:

$$\text{Percent amnesia reversal} = \frac{\text{Drug group} - \text{Base line control group}}{\text{Ceiling control group} - \text{Base line control group}} \times 100$$

The following criteria is used in interpreting the percent of amnesia reversal scores:

40 percent or more (active=A) 25 to 39 percent (borderline=C) and 0 to 29 percent (inactive=N). The duration of the electroconvulsive shock can be varied making the test more or less difficult for a compound to demonstrate an A or C rating. Thus a compound with activity in senile patients and in patients with early memory defects, Piracetam ® [Acta Phychiat. Scand. 54, 150 (1976)], has been administered in this test using the above methodology and 0.2 second and 0.5 second electroconvulsive shock and gave the following results.

| Piracetam ® (mg/kg) | 0.2 sec ECS | 0.5 sec ECS |
|---|---|---|
| 80 | C | N |
| 20 | A | N |
| 5 | C | N |

The inverted U shaped dose response curve is typical of this type of agent.

In addition, the closest compound that could be located in the prior art, 3-phenoxy-2-pyridinecarbonitrile was also tested and proved to be inactive in the above described test.

The following table reports the results for certain compounds of the invention:

Table 1

| | LMC Test | | | | | | |
|---|---|---|---|---|---|---|---|
| | Dose Levels (mg/kg) | | | | | | |
| Compound | 2.5 | 5.0 | 10. | 20. | 40. | 80. | 160. |
| 5-Phenoxy-2-pyridinecarbonitrile | N | A | | A | A | A | C |
| 3-Phenoxy-2-pyridinecarbonitrile | | N | | N | N | | |

The invention is illustrated by the following examples.

EXAMPLE 1 BY PROCESS I

One hundred and eighty six grams of the 3-phenoxypyridine-N-oxide [J. Med. Chem. 14,575 (1971] is melted and with the temperature maintained at 95°–105° C., 128 grams of dimethylsulfate is added dropwise. The mixture is heated at 100° C. for four hours to yield 1-methoxy-3-phenoxypyridinium methosulfate. The 1-methoxy-3-phenoxypyridinium methosulfate is dissolved in 260 ml of water and is added dropwise to a solution of 182 g of sodium cyanide in 400 ml of water under a nitrogen atmosphere at 0° to 5° C. The mixture is allowed to warm to room temperature and is extracted with 1 liter of dichloromethane. The organic solution is dried, concentrated and distilled to yield a mixture of unreacted 3-phenoxypyridine N-oxide, 3-phenoxy-2-pyridinecarbonitrile and 5-phenoxy-2-pyridinecarbonitrile; b.p. 80°–140° C. at 0.1 min. The major product, 3-phenoxy-2-pyridinecarbonitrile is isolated by crystallization from diethylether, m.p. 79°–82° C. 5-Phenoxy-2-pyridinecarbonitrile is isolated by chromatography over Silica gel in toluene. Concentration of the first material eluted produces 5-phenoxy-2-pyridinecarbonitrile; m.p. 84°–85° C. by sublimation.

EXAMPLE 1 BY PROCESS II

A solution of sodium amide is prepared using 5 g of sodium metal in 500 ml liquid ammonia and 0.1 g ferric nitrate catalyst. A solution of 19 g of 2-methyl-5-phenoxypyridine in 20 ml of anhydrous diethylether is added dropwise, followed by a solution of 11 g of n-butylnitrite in 20 ml of anhydrous diethylether. The ammonia is allowed to evaporate and the resulting mixture of solids is treated with 27 g of ammonium sulfate, 100 ml of diethylether and 100 ml of water. The mixture is extracted with 500 ml of dichloromethane. The organic solution is dried, concentrated and the mixture of oximes can be used directly. One isomer is isolated by crystallization from anhydrous diethylether, 5-phenoxy-2-pyridinecarboxaldehyde oxime, m.p. 130°–131° C. To 59 g of reagent thionylchloride is added 5 g of 5-phenoxy-2-pyridinecarboxaldehyde oxime in portions. After the initial exothermic reaction subsides, the solution is refluxed 30 minutes. The solution is concentrated at reduced pressure, is dissolved in 200 ml dichloromethane and is washed until neutral with dilute ammonium hydroxide. The organic solution is dried, concentrated and distilled to yield 5-phenoxy-2-pyridinecarbonitrile, m.p. 84°–85° C., identical by mixed melting point, infrared and proton magnetic resonance spectrum to that prepared by Process I.

EXAMPLE: Pharmaceutical Composition containing 5-phenoxy-2-pyridine-carbonitrile

| Ingredient | Quantity |
|---|---|
| 5-Phenoxy-2-pyridinecarbonitrile | 150 g |
| Lactose | 1038 g |
| Corn Starch | 39 g |
| Hydroxypropyl cellulose | 30 g |
| Magnesium stearate | 7 g |
| Ethanol-water 50:50 | qs |

5-Phenoxy-2-pyridinecarbonitrile, lactose and hydroxypropyl cellulose are blended and granulated with 50:50 ethanol water. The wet granulation is screened, dried and rescreened. The resulting dried granulation is blended with the magnesium stearate and the corn starch, and the mixture is compressed into 225 mg tablets using 11/32 inch standard concave punches. Yield equals approximately 6,000 tablets containing 25 mg of 5-phenoxy-2-pyridinecarbonitrile.

STARTING MATERIAL

2-Methyl-5-phenoxypyridine

A solution of 66 g of potassium hydroxide in 500 ml of diethyleneglycol dimethylether is treated with 110 g of 5-hydroxy-2-methylpyridine and a mixture of water-diethyleneglycol dimethylether is distilled until the temperature of the reaction mixture reaches 164° C. The mixture is cooled to 80° C. and 204 g of iodobenzene is added along with 0.2 g copper-bronze powder and the mixture is stirred and refluxed 16 hours. The mixture is allowed to cool, concentrated in vacuo and is dissolved in 1 liter of toluene. Unreacted 5-hydroxy-2-methylpyridine is removed by passage over a 100 g column of Silica gel in toluene and 2-methyl-5-phenoxypyridine is isolated by distillation at reduced pressure, b.p. 138°–140° C. at 10 mm.

I claim:

1. A compound of the formula

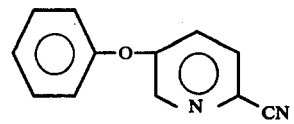

and pharmaceutically-acceptable salts thereof.

2. A compound of claim 1 having the name 5-phenoxy-2-pyridinecarbonitrile hydrochloride.

* * * * *